United States Patent [19]
Barone et al.

[11] Patent Number: 5,311,908
[45] Date of Patent: May 17, 1994

[54] BLOOD PROCESSING METHOD AND APPARATUS WITH DISPOSABLE CASSETTE

[75] Inventors: David Barone; Russell Herrig, both of Sharon; Joseph M. Medberry, Seekonk; Paul M. Volpini, Quincy; Joseph R. Plante, Ashland, all of Mass.

[73] Assignee: Haemonetics Corporation, Braintree, Mass.

[21] Appl. No.: 992,057

[22] Filed: Dec. 17, 1992

Related U.S. Application Data

[63] Continuation of Ser. No. 727,663, Jul. 9, 1991.

[51] Int. Cl.⁵ .......................... B04B 11/00; F16K 1/00
[52] U.S. Cl. ........................ 137/881; 73/865.9; 251/7; 494/10; 494/37
[58] Field of Search .................. 494/37, 1, 2, 5, 7, 494/10; 137/881, 883; 251/7; 73/863.01, 865.9, 597; 340/603, 606, 621; 604/408, 409, 410

[56] References Cited

U.S. PATENT DOCUMENTS

| | | | |
|---|---|---|---|
| 4,416,654 | 11/1983 | Schoendorfer | 494/37 |
| 4,425,116 | 1/1984 | Bilstad | 251/7 |
| 4,428,745 | 1/1984 | Williams | 137/883 |
| 5,082,025 | 1/1994 | Vries | 251/7 |

*Primary Examiner*—Robert W. Jenkins
*Attorney, Agent, or Firm*—Hamilton, Brook, Smith & Reynolds

[57] ABSTRACT

A fluid flow apparatus includes a peristaltic pump rotor mounted to a deck module assembly. A disposable software set is provided which includes a cassette which has a primary flexible tube and a pump platen adjacent to which the primary flexible tube resides. Tubing with blood processing bags are coupled to the manifold along with the input port of the rotor of a disposable blood processing centrifuge bowl. The software set also includes a three-to-one manifold which connects the primary tube to a plurality of secondary flexible tubes. Fluid flow through the secondary flexible tubes is controlled by a plurality of pinch valves which pinch the secondary tubes closed against closing surfaces on the cassette. A deck module assembly allows a user to properly secure the cassette relative to the pump rotor and the pinch valves. A flat surface is provided on the manifold to couple sonic radiation into the manifold and sense the presence of fluids therein.

23 Claims, 14 Drawing Sheets

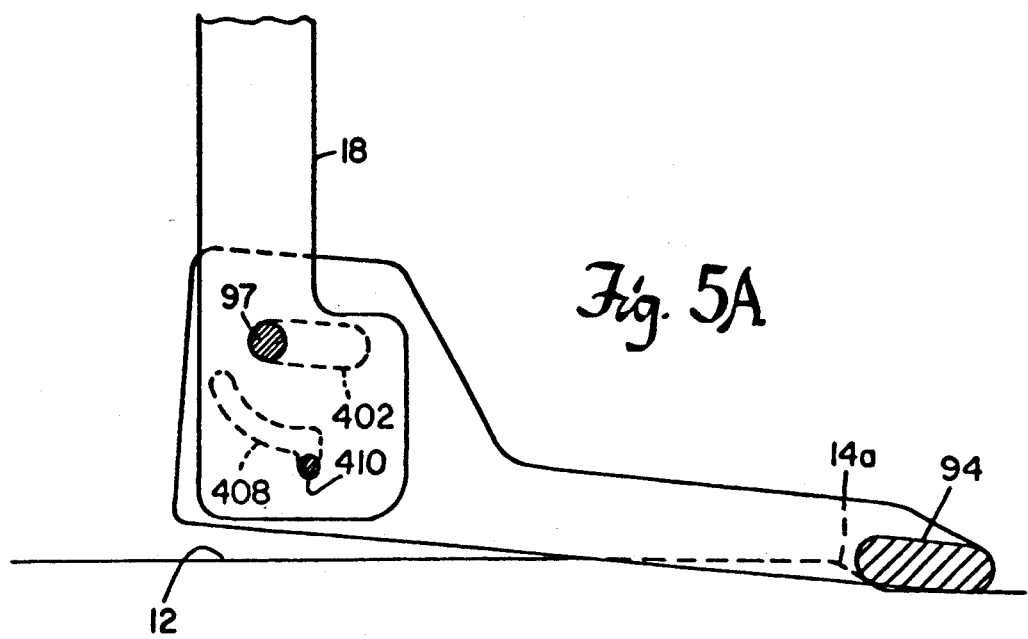
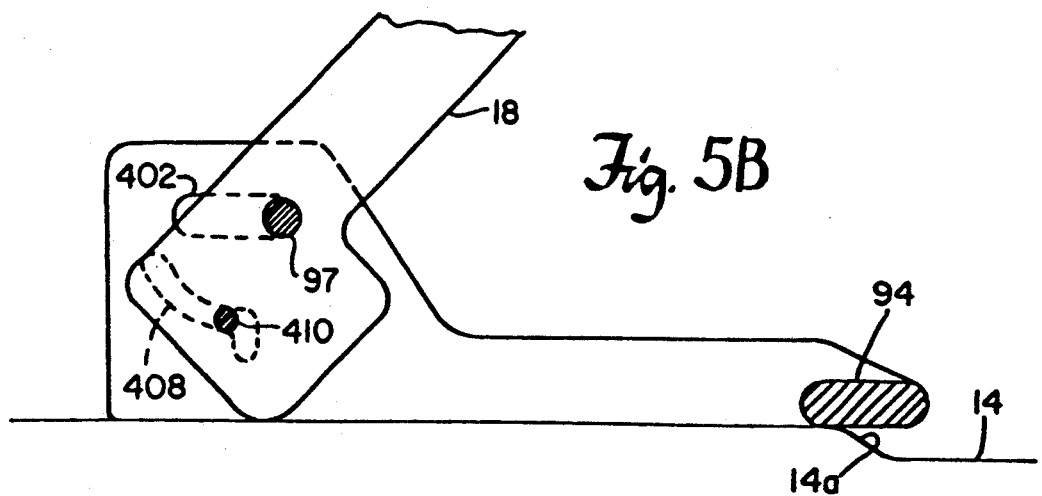
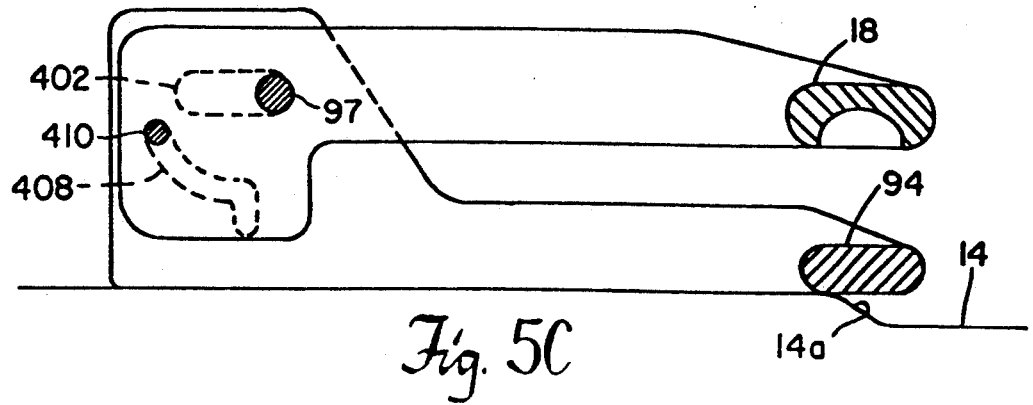

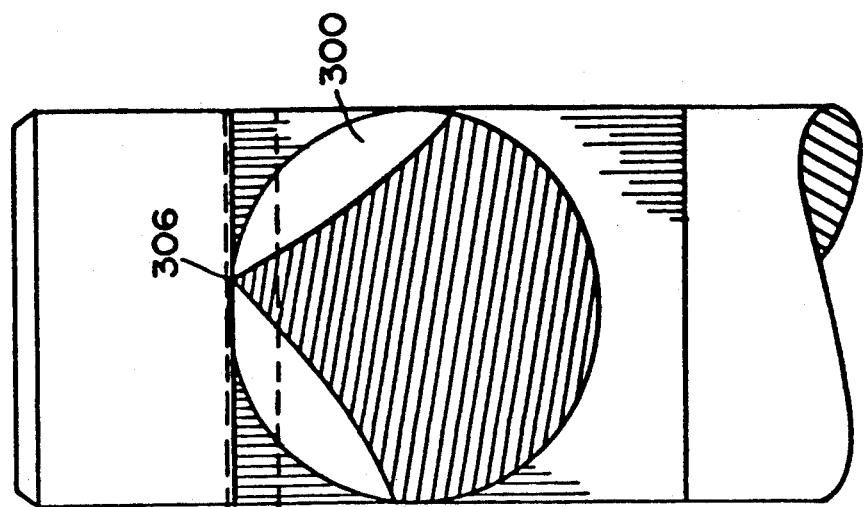
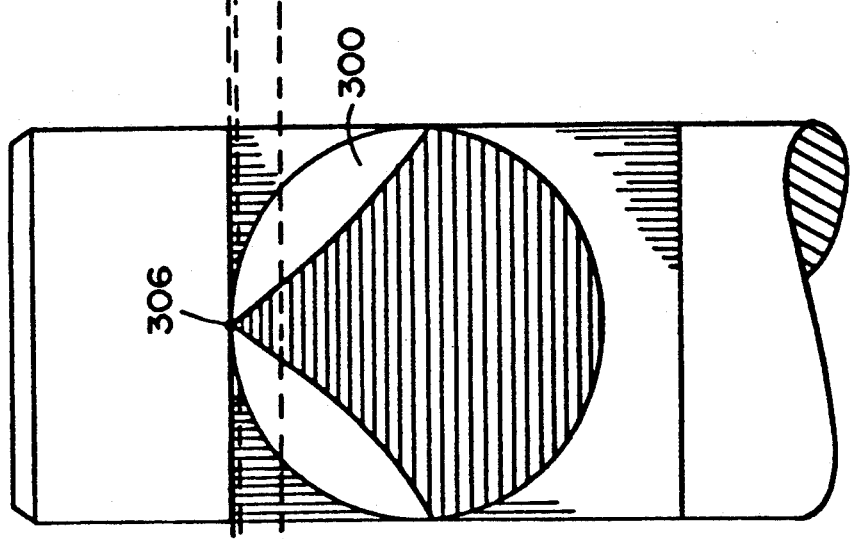
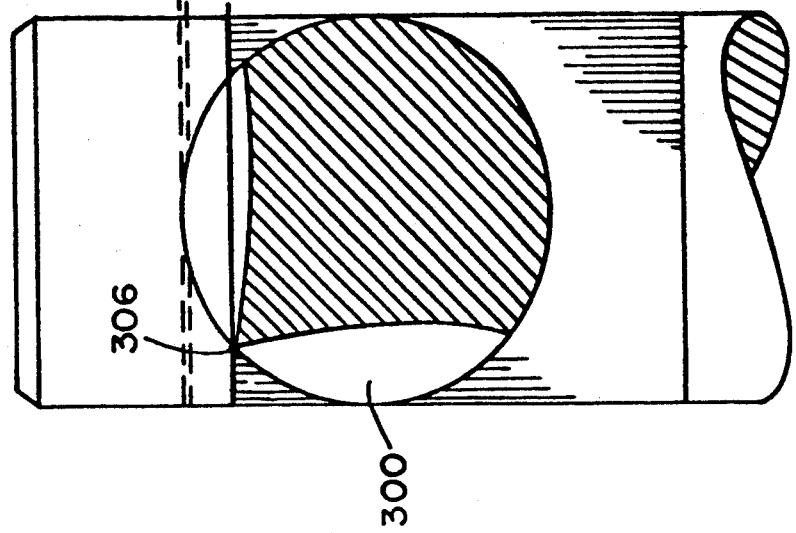

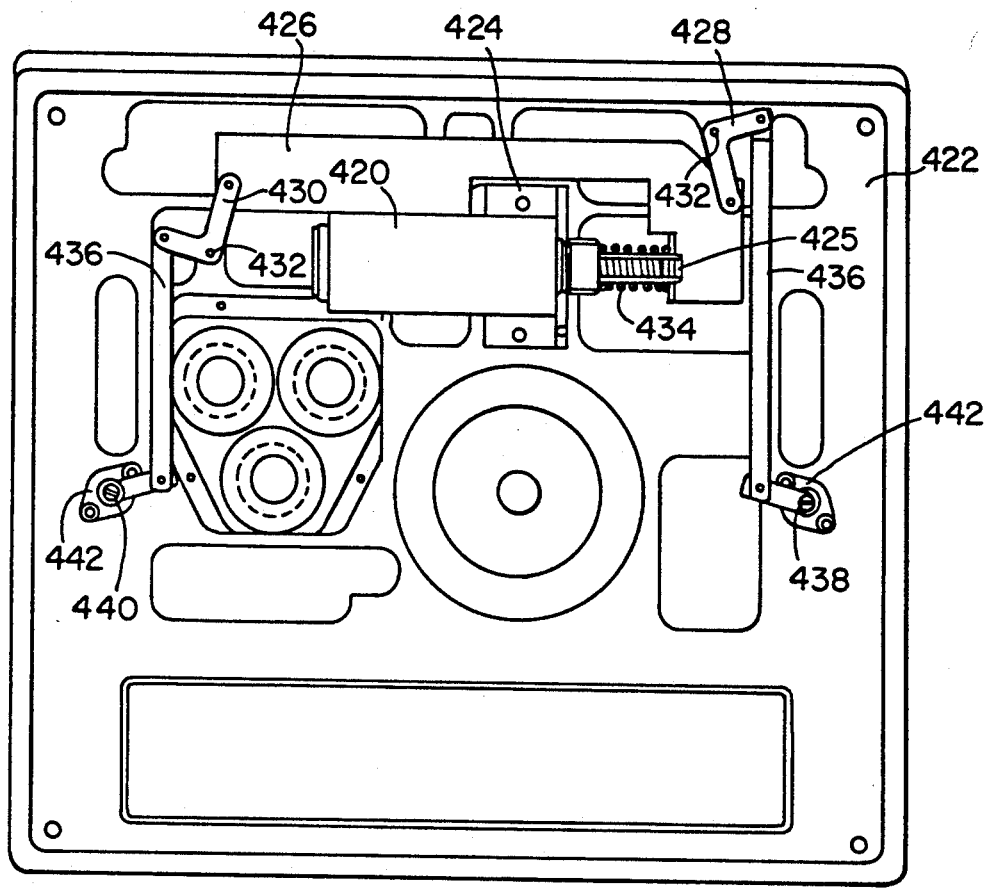
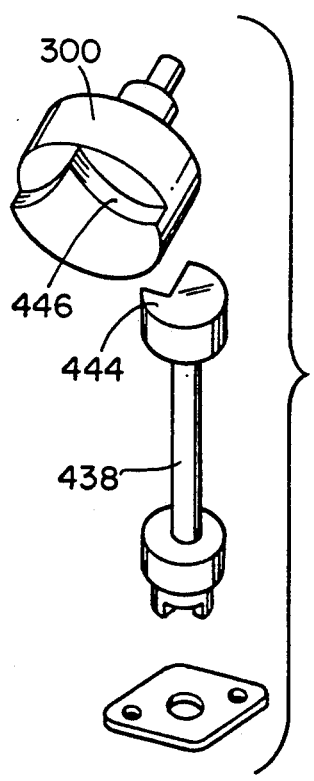
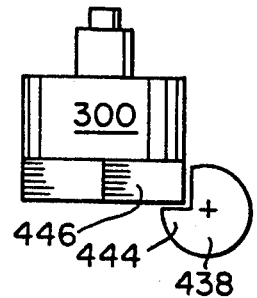
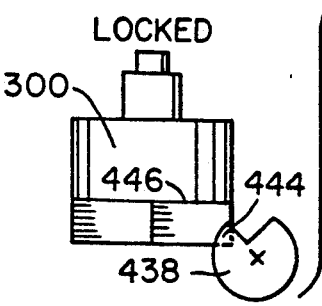
Fig. 8
Fig. 8A
Fig. 8B

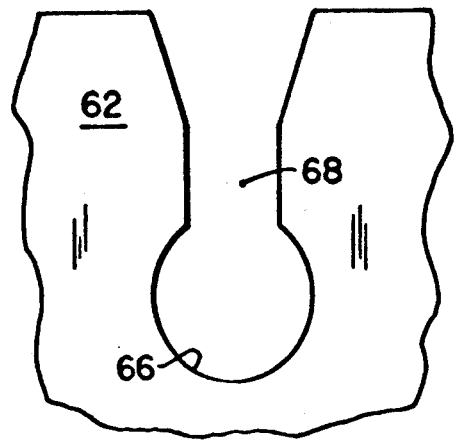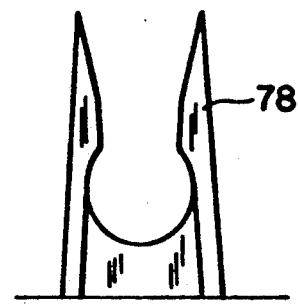
Fig. 10
Fig. 12A
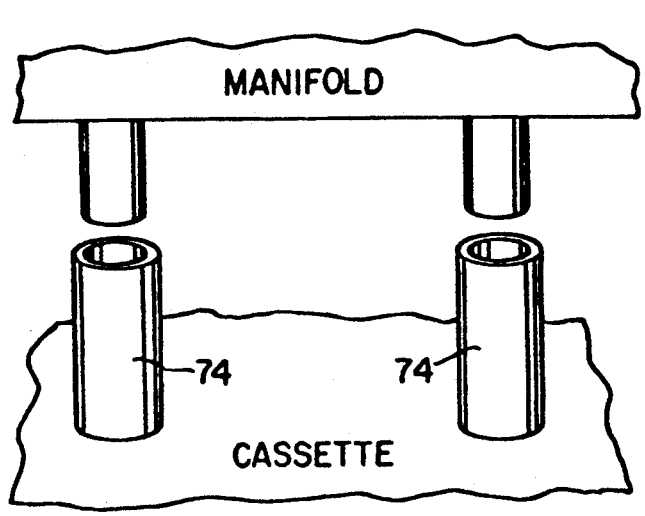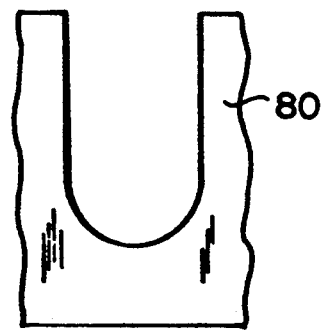
Fig. 11
Fig. 12B

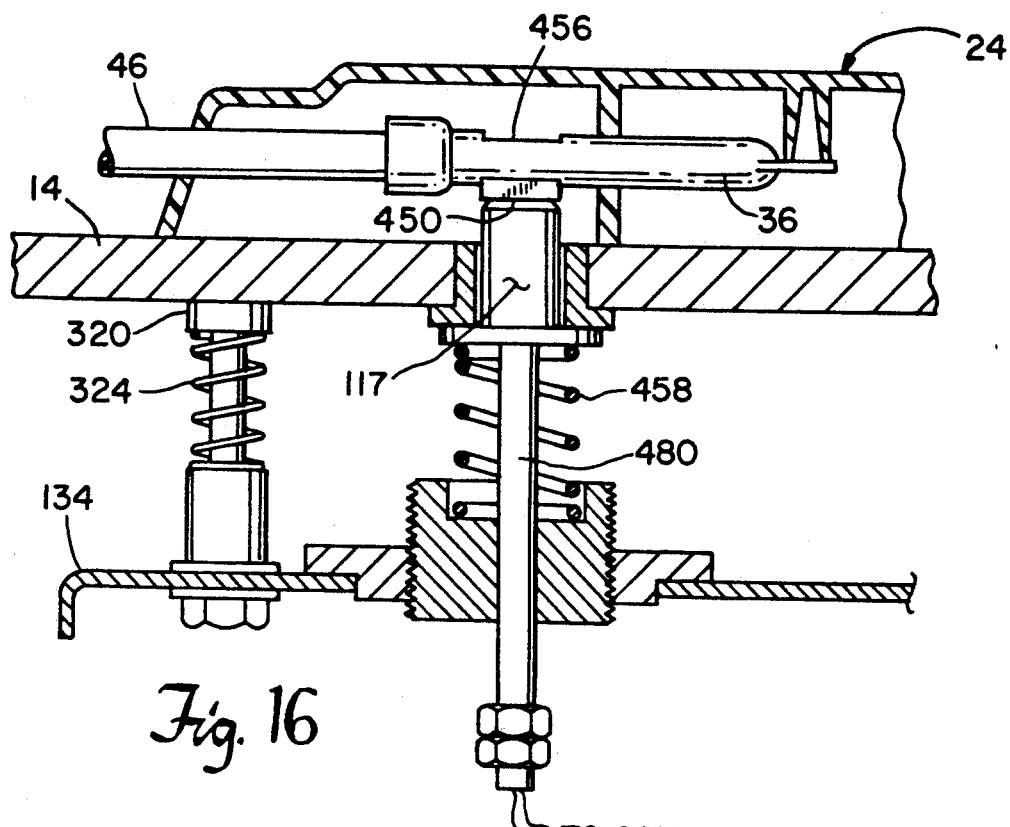
Fig. 16
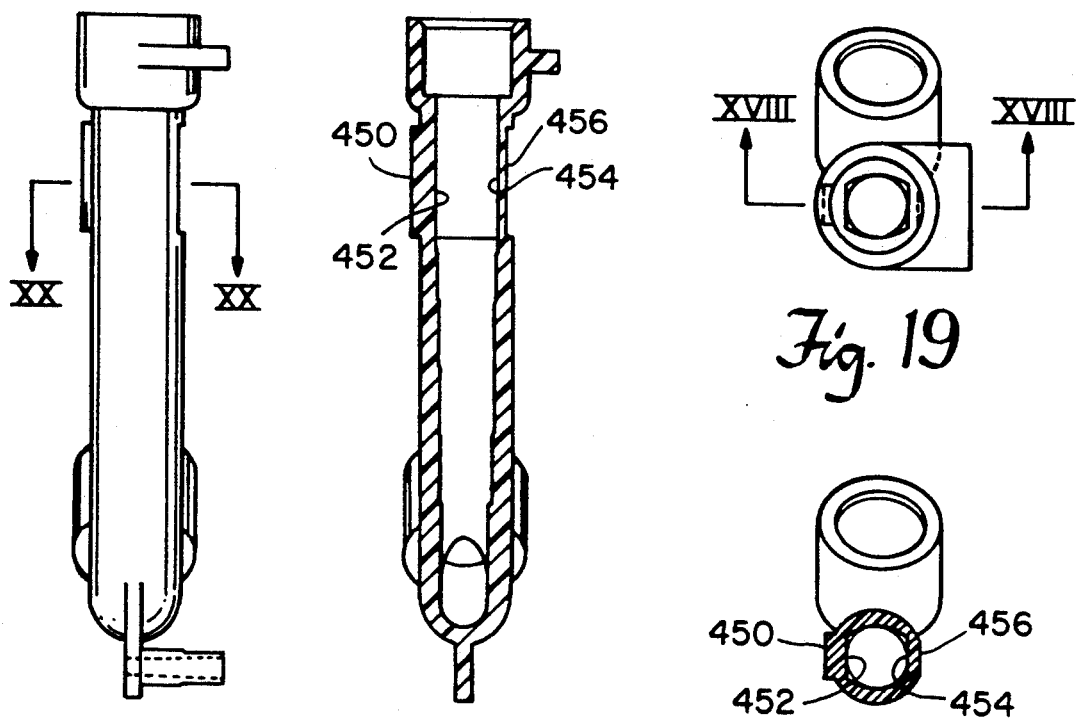
Fig. 17    Fig. 18    Fig. 19
Fig. 20

BLOOD PROCESSING METHOD AND APPARATUS WITH DISPOSABLE CASSETTE

RELATED APPLICATIONS

This is a continuation patent application which claims priority to pending prior application Ser. No. 07/727,663 filed on Jul. 9, 1991.

BACKGROUND OF THE INVENTION

A substantial volume of blood is shed during many major surgical procedures, such as heart by-pass surgery and hip replacement surgery. Often the shed blood, which has been contaminated, is discarded and replaced with donor blood. An alternative procedure has been developed in which the shed blood is recovered, the contaminants removed, and the "uncontaminated" blood cells reinfused into the patient.

In this procedure, the fluid in the surgical site is collected using suction and is drawn into an evacuated reservoir. The fluid collected in the reservoir, called "shed blood", contains whole blood, saline used to rinse the surgical site, blood clots, bone chips, fatty tissue, anti-coagulants and other miscellaneous contaminants.

The collected shed blood may be disposed of in at least three ways. First, it may be discarded and the lost blood volume replaced by donor blood.

A second alternative is to filter the shed blood and transfuse it to the patient. The filter removes blood clots, bone chips and tissue from the shed blood, but the filtered shed blood remains diluted with the saline originally used to rinse the surgical site.

The third alternative is to "wash" the shed blood, as well as filter it. One way of washing shed blood is to use a centrifugal wash system. (See "The Preparation of Leukocyte-Poor Red Blood Cells: A Comparative Study", Meryman et al., *Transfusion* 20(3):285:287 (1980).) In a typical centrifugal wash system, shed blood is centrifugated while washing it with saline in a disposable centrifuge bowl or rotor. A typical bowl for such a system is the so-called Lathan bowl, shown in U.S. Pat. No. 4,300,717. Since red cells have a higher density than saline, platelets, white cells or blood plasma, the red cells fill the outermost portion of the rotating centrifuge bowl. As more shed blood enters the bowl, the red cells remain in the bowl displacing the supernatant (saline, plasma, platelets, anti-coagulants, etc.) out of the bowl. Next, saline is directed into the bowl, instead of shed blood. Saline, entering the bowl, is directed by the lower extended skirt portion of the core of the bowl to the outermost radius of the bowl and through the bed of packed red blood cells. In this way, the supernatant is diluted and displaced by the saline until a satisfactory "washout" efficiency is obtained.

The various fluids are directed into and out of the bowl by peristaltic pump(s). The pump(s) comprise a motor driven rotor with rollers disposed opposite a stationary platen. Flexible fluid pathways formed by plastic tubing are occluded between the platen and the rollers. As the pump rotor rotates, the rollers cause the tubing to alternately contract and expand to propel the fluid in the tubing along a desired path. Various sections of the flexible tubing are also opened or closed by hydraulic or pneumatic valves to control the fluid flow.

SUMMARY OF THE INVENTION

An apparatus for regulating fluid flow in a blood processing system (such as a blood washing system) includes a motor driven rotor for a peristaltic pump which has a plurality of rollers disposed about the circumference of the rotor. A disposable cassette houses a flexible tube and manifolds through which fluid flows. The cassette has a curved platen against which the flexible tube resides. The cassette is removably secured to the apparatus such that the flexible tube is in contact with both the platen and rollers of the rotor. A fluid flow is then induced through the tube by rotation of the rotor.

In the preferred embodiment, the flexible tube is a primary flexible tube, and the cassette further includes a manifold which connects a plurality of secondary flexible tubes to the primary flexible tube. This connection allows fluid flow between the primary flexible tube and each of the secondary flexible tubes. A plurality of valving elements are provided. Each element controls the flow of fluid through one of the secondary flexible tubes. In the preferred embodiment, these valving elements are solenoid controlled pneumatically operated pinch valves. The cassette includes closing surfaces, or anvils, against which the pinch valves individually occlude the secondary flexible tubes to restrict the fluid flow through the tubes. The valves are spring biased in a normally-closed position such that with the cassette in place on the working surface, the pinch valves keep the secondary tubes occluded when electrical power to the apparatus is interrupted.

The securing mechanism of the apparatus preferably includes a handle which closes over the disposable cassette, and holds the flexible tube between the rollers of the rotor and the platen of the cassette. A securing mechanism (in the preferred embodiment a drag bar) moves with motion of the handle, and contacts the cassette, drawing it toward the pump rotor as the handle is moved toward the closed position. Side rails and a top rail restrict the motion of the cassette in first and second mutually perpendicular directions when it is positioned on the working surface. Thus, manual force on the handle in a single direction causes the drag bar to contact the cassette and compress it against the pump rotor in a third direction perpendicular to said first and second directions. A locking mechanism which is preferably pneumatically controlled prevents inadvertent opening of the securing mechanism.

The cassette resides on a working surface of the apparatus while it is secured with the securing mechanism. Elements which interact with the cassette, such as the pinch valves and a fluid detector, are secured to a base plate which resides below the working surface. These elements extend through spaces in the working surface to interact with the cassette residing on the working surface. To facilitate removal of the cassette, vertical motion of the base plate, and elements secured thereto, is linked to motion of the handle. As the handle is opened (rotated upward) the base plate lowers causing the elements extending through the working surface to recede below the working surface.

The present invention simplifies loading of a disposable set into a blood washing system by integrating the components into the rigid cassette frame. Since the flexible components (tubes) are incorporated into the rigid cassette frame, a reliable interface is ensured between the tubes and the components on the deck assembly. The loading of the system software is simplified by the cassette and the receiving apparatus of the deck module, which aligns the elements of the cassette with the elements of the deck assembly. Because the pinch valves are in a normally closed position, inadvertent mixing of fluids during a power loss is avoided. A pneumatic locking mechanism which keeps the handle locked in the closed position prevents removal of the cassette while the system is operating. Also, the overall size of the blood washing system is small due to the integration of elements onto the single cassette module.

BRIEF DESCRIPTION OF THE DRAWINGS

FIGS. 5A–5C are detailed side views showing different positions of the handle and the drag bar.

FIGS. 7A–7C are illustrative views of the contact between a cam and a rod of the present invention.

FIG. 8 is a detailed bottom view of the deck assembly showing the pneumatic lock assembly.

FIG. 8A is an isolated view of a cam and handle lock.

FIG. 8B is a top view of the handle lock in both locked and unlocked positions.

FIG. 10 is an isolated view illustrating the shape of a mounting clip as used with the tubes of the cassette.

FIG. 11 is an isolated view illustrating a mounting connection used with the manifolds of the cassette.

FIG. 12A is an isolated view illustrating the shape of a mounting clip as used with the manifolds of the cassette.

FIG. 12B is an isolated view of a semicircular projection used as a support in the cassette.

FIG. 16 is a detailed sectional view of the fluid sensor portion of the system.

FIG. 17 is a side view of the one-to-one manifold 36.

FIG. 18 is a section taken through lines XVIII—XVIII of FIG. 17. FIG. 19 is a top view of the one-to-one manifold 36.

FIG. 20 is a sectional view taken along lines XX—XX of FIG. 19.

DETAILED DESCRIPTION OF A PREFERRED EMBODIMENT

A. System and Disposable Set

Figure 1:
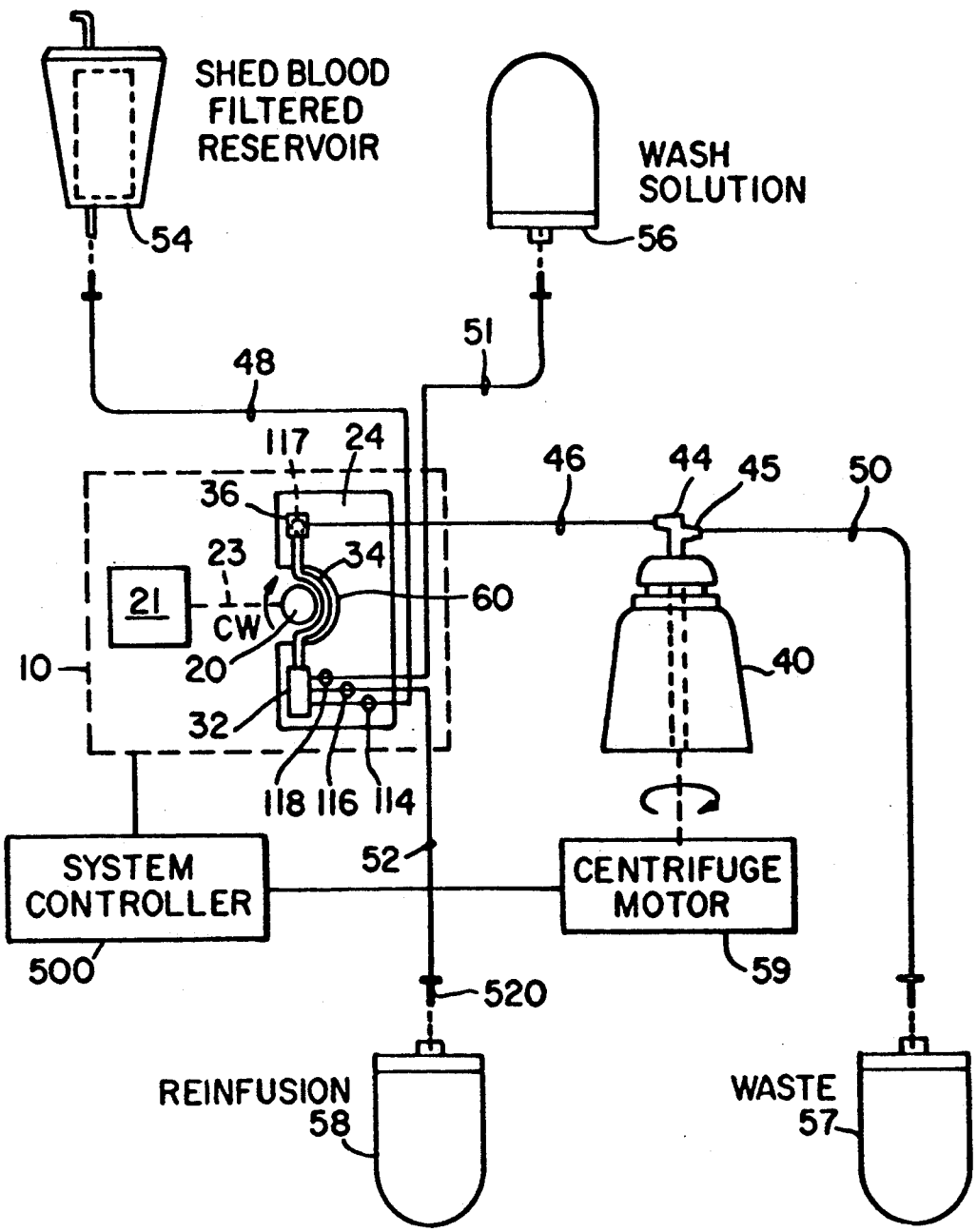
FIG. 1 is schematic illustration of a blood washing system with a disposable cassette incorporated therein.

A system for performing a blood washing cycle is schematically illustrated in FIG. 1. A fluid flow apparatus 10 includes a disposable cassette 24. The cassette is secured in the apparatus 10 such that a primary tube 34 of the cassette 24 is in contact with both a platen 60 of the cassette and rollers (not shown) of a peristaltic pump rotor 20 of the assembly. The primary tube 34 provides fluid connection between a 3-to-1 interconnection manifold 32 and a 1-to-1 manifold 36. Manifold 32 provides fluid communication between primary tube 34 and secondary tubes 48, 51 and 52. Manifold 36 provides fluid communication between tube 34 and centrifuge tube 46, which is connected to the input port 40 of the centrifuge bowl 40. Bowl 40 is a disposable blood processing bowl of the type described in U.S. Pat. No. 4,300,717 and has a stationary input port 44 and output port 55 coupled to the interior of the rotatable bowl by a rotary seal mechanism (not shown). Fluid is moved through the primary tube 34 by rotation of the pump rotor 20. The compression of the flexible tube 34 by the rollers of rotor 20 provides a peristaltic pumping action which moves fluid through the tube 34.

To control which of secondary tubes is in fluid communication with the primary tube 34 at any point in time, solenoid controlled pneumatically operated pinch valves 114, 116, 118 are used to pinch closed the tubes not in use. The valves 114, 116, 118 are spring-biased normally closed, and compress tubes 48, 51, 52, respectively, against anvil closing surfaces formed within the cassette 24. Also, an ultrasonic fluid detector sensor 117 may be inserted through an opening in the deck opposite the location of the one-to-one manifold 36 on the cassette to validate the presence of fluid in the line. The detector 117 is electrically coupled to controller 500. With the fluid connections established as shown in FIG. 1, the blood washing process proceeds as follows.

The pinch valve 114 is opened to allow fluid flow through tube 48 coupled to shed blood filtered reservoir 54, and the peristaltic pump motor 21 is engaged to rotate the pump rotor 20 in a counter-clockwise direction. This causes the rollers of the rotor 20 which are in pressure contact with the tube 34 to induce a fluid flow through the tube. Fluid is thus drawn from the shed blood reservoir 54 in which shed blood collected from a surgical site is stored. The shed and filtered blood flows through tube 48 and tube 34, and is input through tube 46 and port 44 to the centrifuge bowl 40. The bowl 40 is rotated counter-clockwise by motor 59 while being filled, such that the blood is centrifugated into separate constituents. The dense red blood cells are forced to the sidewall of the bowl and are thus separated from the less dense, unwanted constituents in the bowl. The less dense unwanted constituents form an inner layer which is forced out through an inner slot in the top of the bowl which leads to output port 45 and tube 50 and into waste receptacle 57.

Once a preliminary separation is complete, the pump rotor 20 is stopped, and pinch valve 114 is closed. Pinch valve 118 is then drawn into the open position. With the centrifuge bowl 40 rotating, the pump motor 21 is then started once again in the counter-clockwise direction to induce a fluid flow from wash solution bag 56 in which a wash solution, such as saline, is kept. Saline is thus drawn through tube 51, tube 34, tube 46 and input port 44, to arrive in the centrifuge bowl 40. This fluid flow during centrifugating carries out further unwanted constituents from the red blood cells in the centrifuge bowl 40. As this flushing of the red blood cells takes place, the waste overflowing into the waste receptacle 57 is monitored with a fluid detector (not shown). The flushing is maintained until the detector indicates that the free hemoglobin/saline mixture reaches acceptable levels.

Once the blood washing is determined to be complete, the peristaltic motor 21 is stopped and the pinch valve 118 closed. The motor 59 driving centrifuge bowl 40 is then stopped, and pinch valve 116 is opened, allowing fluid flow through tube 52. Motor 21 is then reversed to drive the rotor 20 in a clockwise direction. This induces a fluid flow which draws the washed red blood cells from output port 45 of the centrifuge bowl 40, through tube 46, through tube 34, and finally through tube 52 and reinfusion spike 520 into reinfusion bag 58. The operation of the pump motor 21 is continued until the bowl 40 is emptied. Bag 58 may now be disconnected and the washed red blood cells reinfused into the patient in a separate procedure. The cassette 24, tubing 48, 51, 52, waste bag 57, bowl assembly 40 reinfusion spike 520 and reinfusion bag 58 (FIG. 1) comprise a disposable software set which can be presterilized and provided as a package to the consumer.

B. peck Assembly

Figure 2:
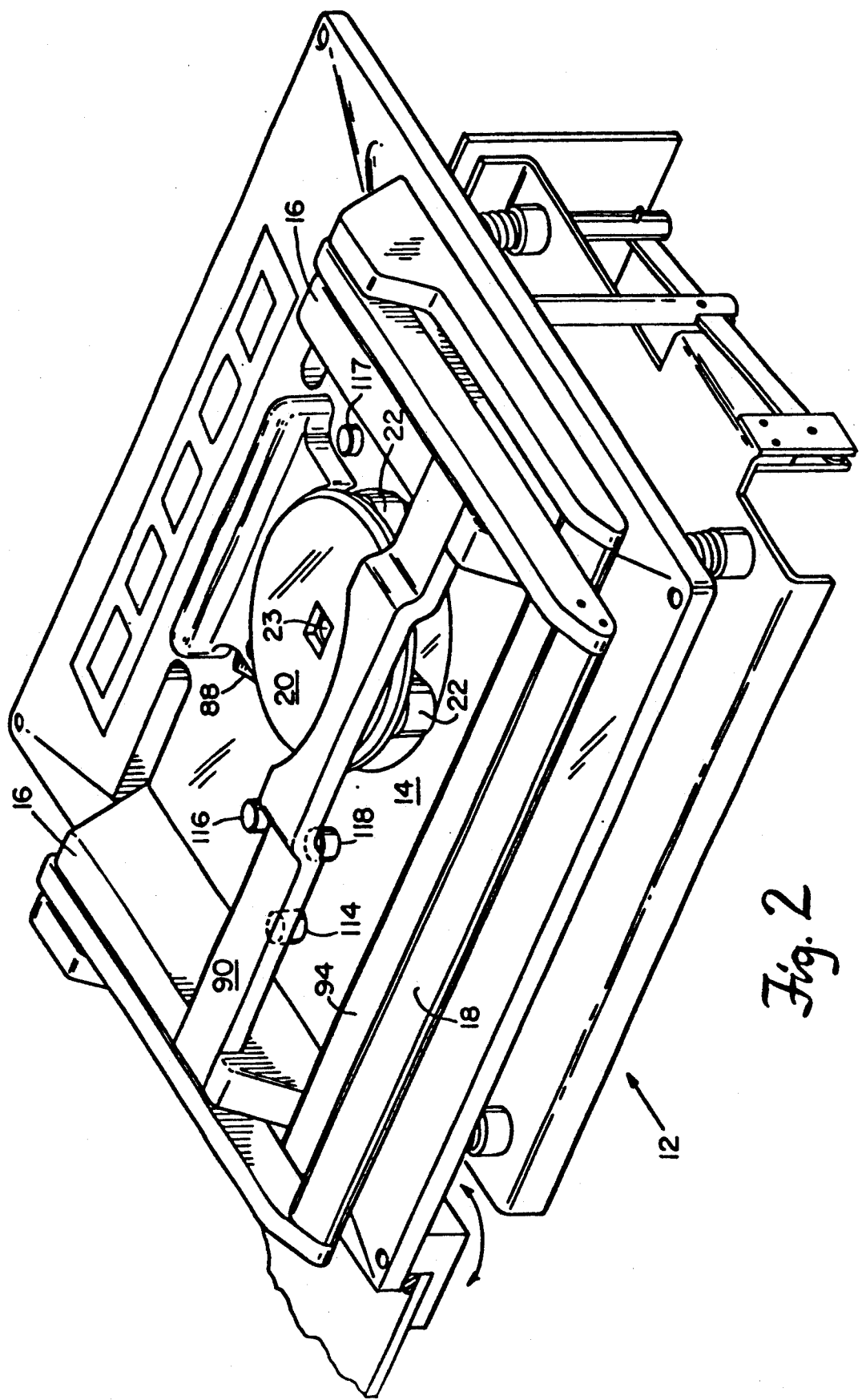
FIG. 2 is a perspective view of the deck module assembly of a fluid flow apparatus of the present invention.

FIG. 2 is a perspective view of a deck assembly 12 of the fluid flow apparatus 10, which has a flat surface 14. Attached to the deck assembly 12 are a pair of side rails 16 to which is pivotably mounted a closing handle 18. Protruding through an opening in the flat surface 14 is peristaltic pump rotor 20. The pump rotor 20 is cylindrical in shape and has three rollers 22, each spaced 120° apart about the circumference of the rotor 20. The pump rotor 20 is attached to a shaft 23, the other end of which is attached to a pump motor 21 (see FIG. 1). The pump motor, when activated, rotates the shaft 23 to turn the pump rotor 20.

Figure 3:
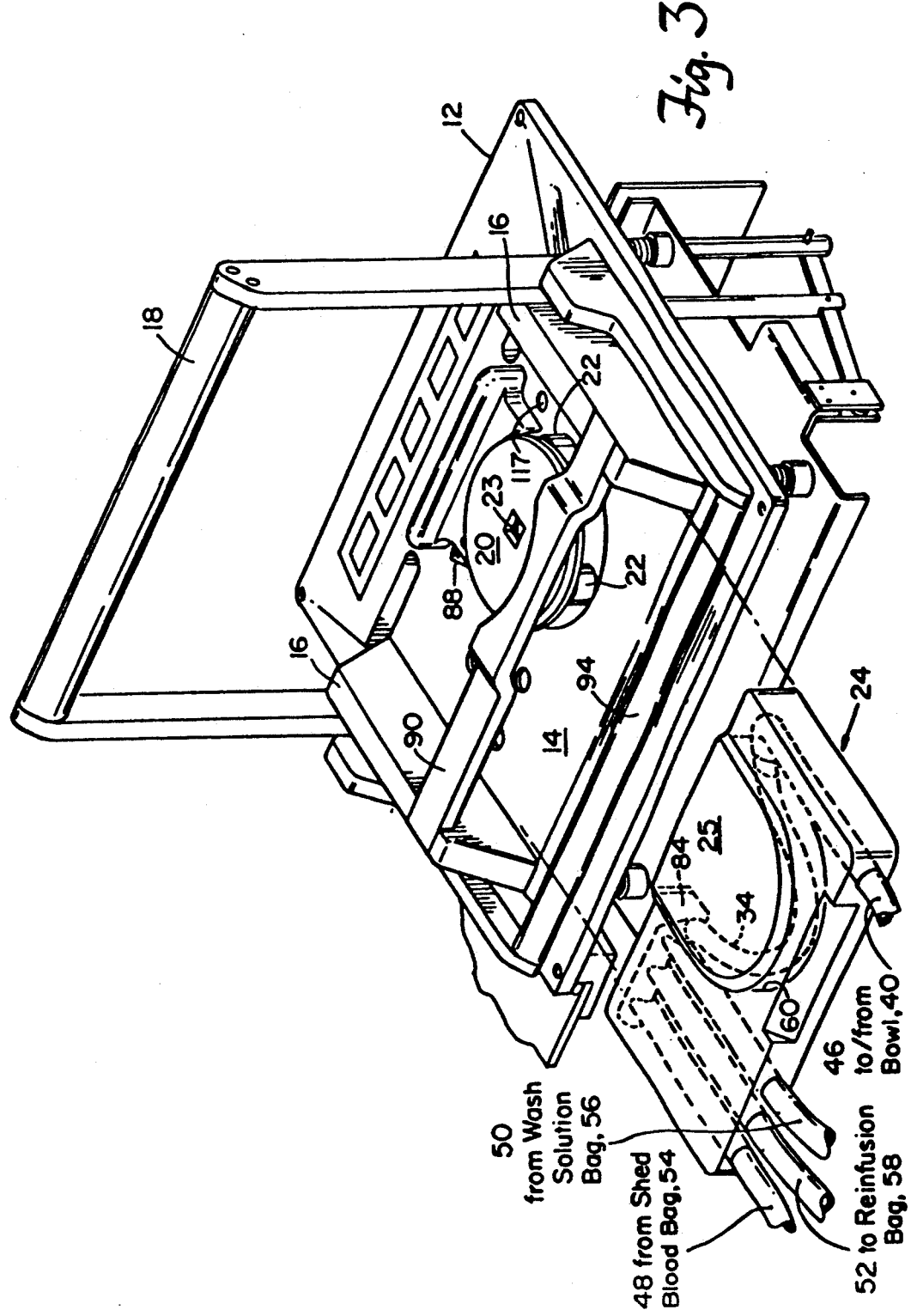
FIG. 3 is a perspective view of the deck module assembly and cassette with the handle in the open position.

Disposable cassette 24 must be secured to the deck assembly 12 during operation. When handle 18 is open (as in FIG. 3) the cassette 24 slides into the space formed by the side rails 16 and pump rotor 20, and under top rail 90, fitting flush against the flat surface 14 of the deck assembly 12. The flexible tubes 48, 51, 52 of the cassette 24 lead from the blood reservoir 54, wash solution bag 56 and reinfusion bag 58, respectively. Raised surface portion 25 of cassette 24 covers the pump rotor 20.

The tube 34 within the cassette 24 is compressed between the cassette platen 60 and the rollers 22 of the pump rotor 20. When the cassette is in this position on the deck assembly 12, inside surface 84 of the cassette depresses spring-biased switch 88. This switch (SW1), when closed, provides a signal to the system controller 500 (FIG. 1) which indicates that the cassette is in place on the deck assembly 12.

With the handle 18 in the open position, drag bar 94 is in a forward position, residing in a lowered portion of surface 14 in the front of the deck assembly. The forward position of the drag bar is such that the top of the front portion of the drag bar is approximately level with the region of the working surface 12 between side rails 16. Thus the cassette 24 slides easily into place onto the working surface without interference from the drag bar 94.

To hold the cassette 24 in place, a user closes the handle 18 over the cassette 24. The handle 18 is rotated forward and downward over the cassette 24. Linkage between the handle 18 and drag bar 94 (discussed hereinafter) causes motion of the drag bar 94 toward the rear of the deck assembly. The drag bar is drawn up a rise in the surface 14, making contact with the cassette and forcing the cassette into firmer engagement with the pump rotor 20 so that tube 34 is securely compressed against the rollers 22 of the rotor. Top rail 90 prevents the cassette from moving upward, and keeps it in place on the surface 14 of the deck assembly 12.

Figure 4:
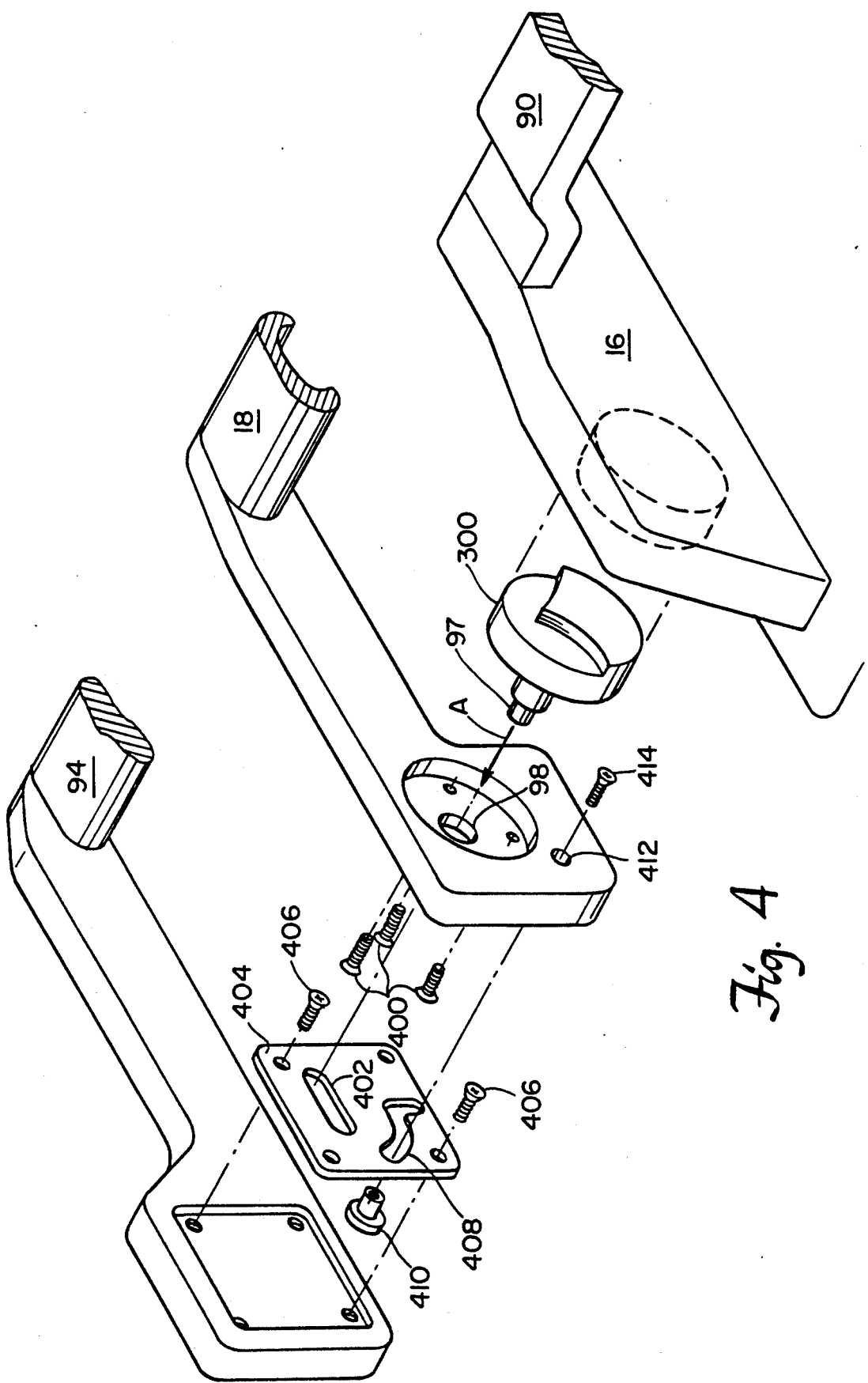
FIG. 4 is an exploded view showing connection between the handle, the drag bar and a side rail.

FIG. 4 is an exploded view showing one side of the connection between handle 18, drag bar 94 and one of side rails 16. Each side of handle 18 is rigidly fixed to a cam 300 by screws 400. Each cam has pin 97 which faces outwardly in the direction of arrow A and passes through a hole 98 in handle 18 and into a straight slot 402 extending horizontally transverse arrow A in drag bar plate 404. The plate 404 is rigidly secured to drag bar 94 by screws 406 (only two of which are shown). A curved slot 408 is also provided in plate 404 and extends vertically downward and horizontally then downwardly. A pin 410 passes through slot 408 and through a hole 412 in handle 18. The pin 410 is secured to the handle by screw 414. Thus, the pin 410 is free to slide in curved slot 408 in response to relative motion between handle 18 and drag bar 94. The pin connections between handle 18 and drag bar plate 404 provide the desired motion of the drag bar 94 in response to manual movement of the handle 18. This motion is demonstrated by FIGS. 5A-5C. It will be understood that although only one side of the connection is shown, the other side is similarly connected.

Figure 6:
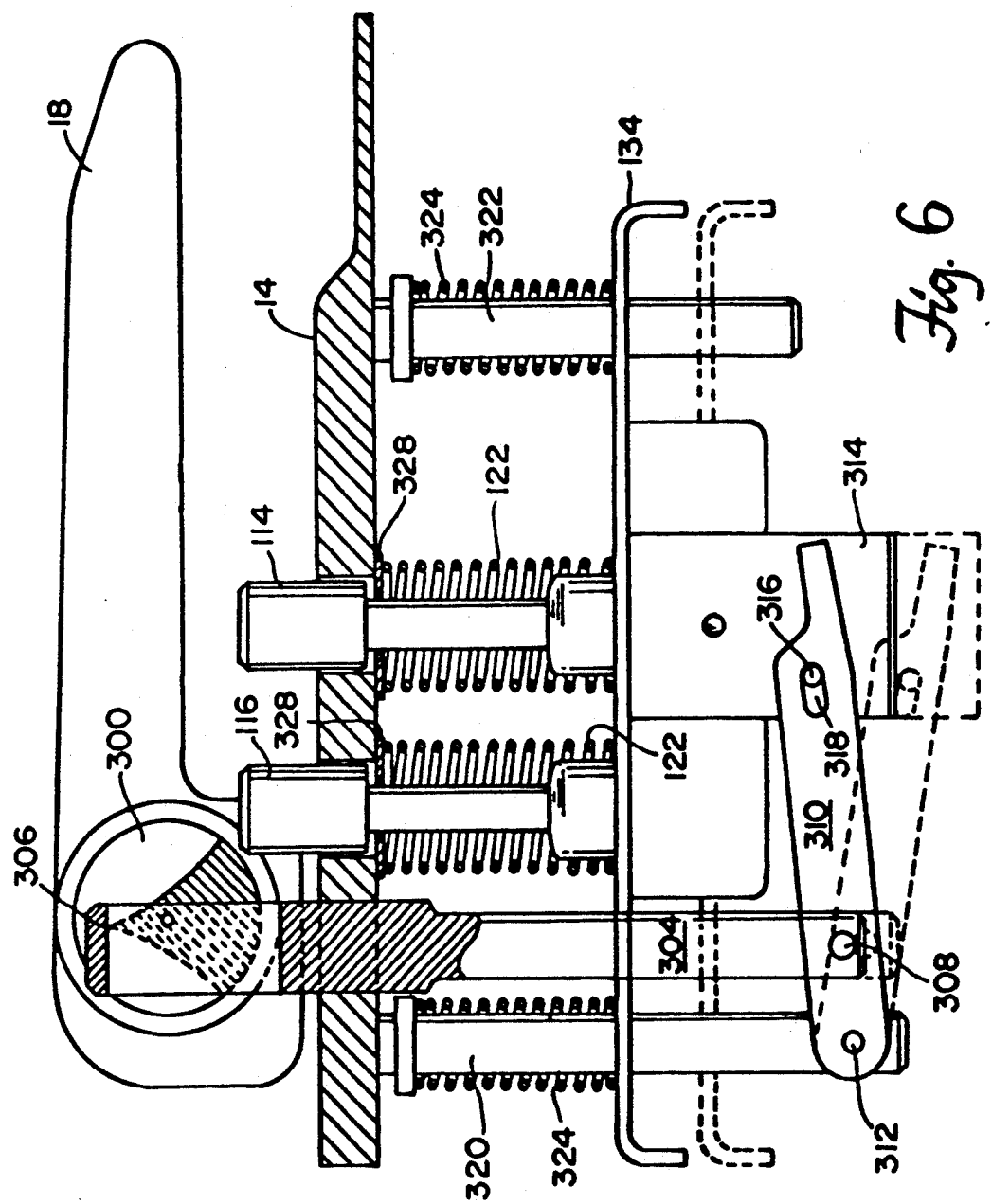
FIG. 6 is a detailed side view of the deck assembly.
Figure 6A:
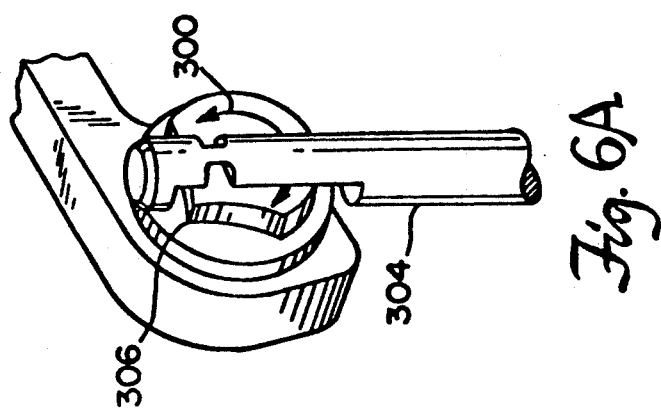
FIG. 6A is an isolated perspective view of a cam/rod connection of the deck assembly.

FIG. 5A shows the handle 18 in an upright position. In this position, pin 97 is in the rear-most portion of horizontal slot 402. As the handle is moved forward, the pin 97 moves in the slot 402 toward the front of the deck assembly 12. Since the distance between pin 97 and pin 410 is fixed, the drag bar 94 moves toward the rear of the deck assembly. As demonstrated in FIG. 5B, the front of the drag bar 94 moves up a rise 14(a) on the surface 14 of deck assembly 12. With a cassette (not shown) in place on the working surface, the drag bar 94 makes contact with the front of the cassette 24 and compresses the cassette 24 into the pump rotor 20 (also not shown). This motion of drag bar 94 is complete when the handle 18 reaches an angle of about 45° relative to the working surface 14. At this point, pin 97 is at the front of slot 402, and pin 410 has risen in the lower portion of slot 408. Since the upper portion of slot 408 is arcuate about the position of pin 97 shown in FIG. 5B, further motion of handle 18 to the lowered position of FIG. 5C causes pin 410 to ride further up in slot 408, but causes no more motion of drag bar 94. As shown in FIGS. 6 and 6A, this further rotation of the handle causes rotation of cam 300 to raise the base plate 134 of the apparatus to bring elements on the base plate 134 through the working surface to contact the cassette 24 already in place.

FIG. 6 is a detailed side view showing base plate 134 and handle 18, to which is attached cam 300. The isolated perspective view of FIG. 6A shows the connection between cam 300 and rod 304. It will be understood by those skilled in the art that one cam/rod arrangement is located to either side of the rear of handle 18, making a symmetrical arrangement for lifting base plate 134, to which elements that protrude through the surface 14 of deck assembly 12 are attached.

Rod 304 has a lip 305 which engages the cam surface 301 of cam 300 and moves in response to rotation of the cam. As shown, the cam has a semicircular shape with a cutaway cam surface portion consisting of two inwardly curved portions which meet at peak 306 of the cam 300. As handle 18 is rotated, the lip 305 of rod 304 moves along this cutaway portion, and rides up and down in the vertical direction. The lower end of the rod has a pin 308 which is connected to arm 310. Arm 310 is connected to a fixed pivot point at pin 312. When the rod 304 moves vertically in response to rotation of the cam 300, the arm 310 is rotated about pin 312.

One arm 310 is located to either side of base plate 134. Motion of the handle 18 causes rotation of the cams 300 positioned to either side of the handle. This, in turn, translates to vertical motion of rod 304 and base plate 134, which is attached to each arm, 310. Each cam has the same cutaway, oriented in the same manner, such that both sides of the base plate 134 move together smoothly. Each arm 310 is connected to a support bracket 314 via a pin 316. The pin 316 fits in a slot 318 of the arm, such that as the arm moves with vertical motion of the rod 304, the pin 316 slides in the slot to allow the rotational motion of the arm 310 to be converted to vertical motion of the base plate 134. In FIG. 6, the lower position of the base plate 134, rod 304 and arm 310 is shown in dashed lines, while the solid lines indicate the upper position (handle 18 lowered).

To maintain the horizontal position of the base plate 134, guide shafts 320, 322 are provided. The shafts are rigidly fixed to the deck assembly surface 14, two shafts 320 being toward the rear of the deck assembly and two shafts 322 being toward the front. Each of the shafts 320, 322 pass through a hole in the base plate such that the motion of the base plate 134 is guided by the shafts, thus limiting the base plate to vertical motion only. A spring 324 is mounted about each of the shafts. These springs exert force between the base plate 134 and the deck assembly surface 14. This force tends to keep the base plate 134 away from the deck assembly surface 14, and therefore urges the handle 18 toward the upright position. The rotation of the handle downward overcomes the force of springs 324 to raise the base plate to the proper position when the cassette is in place. The force of springs 324 is made large enough that they urge the base plate 134 to the lower position. However, the force of the springs is easily overcome by manual force moving the handle 18 into the lowered position (base plate 134 raised).

Springs 122 encircle pistons 129 of pinch valves 114, 116 providing spring force between the base plate 134 and spring nuts 328. A spring 122 is compressed when its pinch valve 114, 116, 118 is pneumatically drawn into the open position. Pinch valve 118 and fluid level detector 117 are not shown in FIG. 6, but it will be understood that these elements are also fixed to the base plate 134 and protrude through the deck assembly surface 14 when the handle 18 is in the closed position. Details of fluid detector 117 will be provided in connection with FIGS. 16-20.

Interaction between can 300 and rod 304 is described in more detail with reference to FIGS. 7A-7C. The slots 318 of arms 310 (FIG. 11) restrict the vertical motion of the base plate 134. When pin 316 is in the rear most portion of the slot 318, the base plate 134 is prevented from further motion downward. FIG. 7A shows the point of contact at which cam peak 306 first engages the lip of rod 304. At this point the angle of the handle relative to the surface 14 of deck assembly 12 is approximately 45°. Further counter-clockwise motion of the cam 300 from the position of the cam in FIG. 7A brings the cam peak 306 out of contact with the lip of rod 304. At this point the rod is restricted from further downward motion because the pin 316 is as far to the rear of slot 318 as possible.

As the handle is rotated downward, the cam 300 rotates clockwise such that the cam peak 306 engages the lip of the rod 304, forcing the rod upward. (Similarly, on the opposite side of the handle 18, the cam 300 is rotated counter-clockwise, forcing its respective rod upward in synchronism with the rod shown in the figures). The maximum lift provided by cam 300 is shown in FIG. 7B wherein the base plate 134 is level, and at its highest vertical position. At this position, each of the pinch valves 114, 116, 118 and the fluid sensor 117 protrude through the surface 14 of the deck assembly. Although the cans 300 are in the maximum lifting position in FIG. 7B, the force of springs 324 tends to urge the cams 300 away from this position, making it inherently unstable. In order to ensure that the handle stays closed when it is in its downward position over the cassette 24, the cam peaks 306 are allowed to ride a distance beyond the maximum lift position, as shown in FIG. 7C. Thus, the position of the rods 304 and the base plates 134 is lowered slightly until the handle 18 is stopped, (by its cam track). In this position, the force of springs 324 tends to keep the handle position stable, preventing the cam peak 306 from riding back past the maximum lift position. Therefore, the handle 18 stays closed over the loaded cassette 24.

In addition to the features of the cam/rod assembly which keep the handle in a closed position, a solenoid controlled pneumatic lock is also provided to keep the handle from being accidentally raised while the unit is operating. Like the other solenoid valves 106, 108, 110, handle valve 112, which controls the handle pneumatic lock cylinder, is operated by the system controller 500 of the unit (See FIG. 13).

FIG. 8 is a detailed bottom view of the deck assembly showing the pneumatic handle locking assembly of the present invention. When the blood processing unit is operating, the controller 500 of FIG. 1, or FIG. 13, opens valve 112 (shown in FIG. 13) to allow compressed air to pass through line 127 to the pneumatic cylinder 420 of the handle lock. The pneumatic cylinder is secured to a support plate 422 on the underside of the deck assembly 12 by cylinder mounting bracket 424. A shaft 425 of the pneumatic cylinder 420 extends from the cylinder chamber and connects to drive link 426. The drive link 426 is connected at either side to pivot links 428, 430. Each pivot link is connected to the support plate 422 at a pivot point 432. Thus, movement of the drive link 426 causes each pivot link 428, 430 to pivot about its respective pivot points 432.

The lock assembly, as shown in FIG. 8, is in the unlocked position. The lock assembly remains in the unlocked position when there is no power to the system due to the force of return spring 434 which surrounds the shaft 425 of the pneumatic cylinder 420. However, when the solenoid valve 112 (FIG. 13) is opened, compressed air to the pneumatic cylinder 420 causes the cylinder 420 to draw shaft 425 into the body of the cylinder against the force of spring 434. The shaft 425 is secured to the drive link 426, and when it is drawn into the body of the cylinder 420, the drive link 426 is forced to follow the movement of the shaft 425 (toward the left hand side of FIG. 8). This movement of drive link 426 causes the pivoting of pivot links 428, 430. Pivot link 428 pivots about its pivot point 432 in a clockwise direction, while pivot link 430 pivots about its pivot point 432 in a counter-clockwise direction (when viewed from the bottom view of FIG. 8).

Each pivot link is pivotably secured to a connecting arm 436. Since the pivot links 428, 430 pivot in opposite directions, both cause their respective connecting arms to move parallel to the sides of the deck assembly toward the rear of the deck assembly (toward the bottom of FIG. 8). This movement of connecting arms 436 causes handle locks 438, 440 to be rotated. Each handle lock is mounted in a lock retainer 442 which allows the lock to rotate. The movement of the connecting arms toward the rear of the deck assembly causes handle lock 438 to rotate counter-clockwise and handle lock 440 to rotate clockwise (when viewed from the bottom view of FIG. 8). If the handle is in the closed position when the pneumatic cylinder causes the rotation of the handle locks 438, 440 via connecting arms 436, the head of each handle lock 438, 440 rotates to engage a cam 300 (of FIGS. 4, 6, 6A, 7A–7C, 8A and 8B) to prevent the cam from moving away from the "handle-closed" position. This locking action is more clearly shown in FIGS. 8A and 8B.

FIG. 8A is an isolated view of handle lock 438 and one of cams 300 which move with the handle 18. Handle lock 438 is like handle lock 440, but rotates the opposite way to engage its cam 300. When the handle 18 of the deck assembly is in the lowered position, the cam 300 to the right side of deck assembly 12 is in its fully clockwise-rotated position. Thus, to open the handle from this position, the cam 300 shown in FIG. 8A would have to be rotated in a counter-clockwise direction. The handle lock 438 has a lip which lies adjacent the lip 446 of the cam 300. When the connecting bar linkage of the lock assembly shown in FIG. 8 causes the handle lock 438 to rotate clockwise (due to activation of the pneumatic cylinder), the lip 444 of the handle lock 438 rotates toward the body of cam 300 to lie adjacent lip 446 of the cam 300. This positioning of the lip of the handle lock prevents the rotation of the cam 300 in a counter-clockwise direction, thus preventing the handle from being opened.

A top view of the lock assembly is shown in FIG. 8B in both the unlocked and locked positions. As shown in FIG. 8A, the positioning of the handle lock 438 when the pneumatic cylinder is not activated is such that it does not obstruct the cam 300, and the handle 18 of the deck assembly is therefore free to move. However, rotation of the handle lock by activation of the pneumatic cylinder 420 by the system controller 500 causes the lip 444 of the handle lock to move against the lip 446 of the cam 300, as shown in the locked position of FIG. 8B. This positioning of the handle lock prevents the rotation of the cam 300, and therefore locks the handle 18 of the deck assembly in place. It will be recognized by those skilled in the art that the handle lock 440 on the left side of the deck assembly operates in a manner symmetrical to that shown in FIG. 8B to restrict the rotation of the opposite cam 300. Since both handle locks 438, 440 move in unison, both cams, and therefore both sides of the handle, are locked at the same time.

C. Cassette

Figure 9:
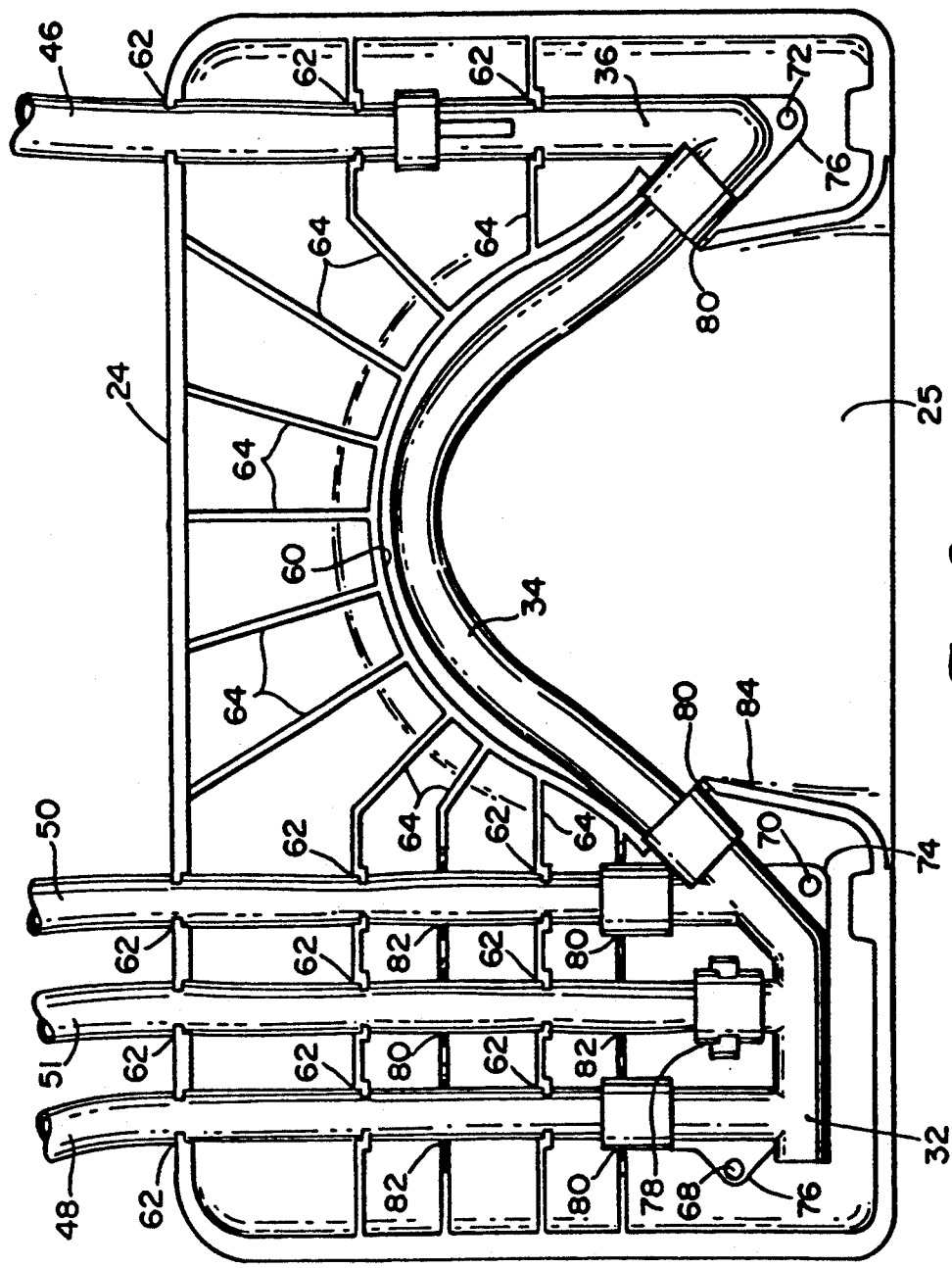
FIG. 9 is a bottom view of the disposable cassette of the present invention.

Details of the organization of the flexible tubes in the cassette 24 are provided in FIG. 9, which is a bottom view of the cassette. Each of the tubes 48, 51, 52 enter the cassette 24 along one side of the plastic, transparent cassette housing 27. The centrifuge tube 46 enters the cassette housing from the same direction, but toward an opposite side of the cassette 24. As will be shown in more detail, the structure of the cassette 24 and deck assembly 12 enables the consumer to quickly and reliably mate the software set (described in connection with FIG. 1) with the hardware, avoiding the cumbersome task of threading the tubing through the peristaltic pump rollers, over the correct pinch valves, and over a fluid detection sensor.

Tubes 48, 51, and 52 are connected to three-to-one manifold 32. The manifold 32 is also connected to flexible tube 34. Flexible tube 34 provides fluid communication between manifold 32 and one-to-one manifold 36. The one-to-one manifold 36 connects tube 34 to flexible tube 46 which exits the cassette 24 leading to centrifuge bowl 40. The shape of manifold 32 and manifold 36, and the positioning of the manifolds 32, 36 in the cassette are such that the connection of tube 34 to the manifolds 32, 36 forces the tube 34 into an arcuate shape. The tube 34 is rigidly bonded to each manifold 32, 36, and is positioned such that its arcuate path keeps it lying adjacent platen surface 60 of the cassette 24. The arcuate shape of the cassette platen 60 is greater than 120° and the rollers 22 of the pump rotor 20 are spaced apart by 120°. Therefore, the tube 34 is always being compressed by at least one roller 22 at any point during rotation.

In the preferred embodiment, the disposable cassette 24 is formed of injection-molded plastic, and includes all the components necessary to retain manifolds 32, 36 and tubes 46, 48, 51, 52. Molded in the plastic cassette 24 are mounting clips 62. The clips 62 are located in different parts of the cassette 24, and are positioned to hold the tubes 46, 48, 51, 52 in the desired orientation. Each of the clips 62 is formed in one of ribs 64 of the cassette 24, or in the side of the cassette through which tubes 46, 48, 51, 52 exit the cassette. The ribs 64 are formed in the cassette 24 during the injection molding process, and provide lateral support to the cassette to prevent accidental failure or breakage of the cassette 24. As shown, each of the ribs 64 emanates from the platen surface 60, and terminates at one of the outer walls of the cassette 24. The ribs 64 thus provide support to the platen 60 when pressure is applied by the pump rotor 20 which squeezes the tube 34 between the rotor 20 and the platen 60. The clips 62 of the cassette are formed as grooves in the ribs 64 in locations at which a tube 46, 48, 51, 52 is to be retained.

An isolated side view illustration of one of the clips 62 is shown in FIG. 10, to demonstrate the shape and functionality of the clips. As shown, the clip 62 has a rounded portion 66 which has a diameter just slightly larger than the outer diameter of one of the tubes 46, 48, 51, 52. Thus, a tube fits in the rounded portion without the flow of fluid in the tube being restricted. However, to get the tube into the rounded portion of the clip 62, it must be wedged through the narrow slot 68 of the clip 62. Since the tubes are flexible, manual pressure on the tube is used to force the tube to temporarily flatten while it is being inserted into the clip through the narrow slot. Once the flexible tube is in the rounded portion 66, it returns to its normal cylindrical shape, and is held tightly within the clip. Thus, the tubes are removably retained in the clips 62. The manifolds 32, 36 are fixed to the cassette in the positions necessary to connect them properly to tubes 46, 48, 51, 52 when the tubes are mounted in the cassette by the mounting clips. To fix the manifolds 32, 36 in their respective positions in the cassette, mounting pins are formed on the manifolds. Since the manifolds 32, 36 themselves are preferably injection molded plastic, the forming of the pins is a simple manufacturing task. As shown in FIG. 9, the three-to-one manifold 32 has two mounting pins 68, 70, while the one-to-one manifold 36 has only one pin 72. The holes which receive the mounting pins are formed in cylindrical projections 74 extending from the surface of the cassette 24. This relationship is demonstrated by the isolated illustrative view of FIG. 11. Each of the pins 68, 70, 72 is formed on a flange 76 extending from its respective manifold 32, 36. The travel of a pin into a cylindrical projection 74 is restricted by the contact of the flange on which the pin is mounted with the cylindrical projection 74. Thus the locating of the flanges on the manifolds 32, 36 in part determines the distance of the manifolds from the cassette surface.

The relative orientation of the manifolds 32, 36, the tubes 46, 48, 51, 52, and the cassette 24 is important to prevent any unnecessary bending of the tubes connecting to the manifolds 32, 36. Thus, the distance from the surface of the cassette is approximately equal for each of the manifolds and tubes mounted in the cassette 24. For the tubes 46, 48, 51, 52 this distance is determined by the distance between the cassette surface and the circular portions 66 of the mounting clips 68, as well as by the distance between the cassette surface and the manifolds to which the tubes connect. The distance between the manifolds 32, 36 and the cassette surface is determined first by the height of the cylindrical projections from the cassette surface. This distance is also determined by several supports extending from the surface of the cassette 24, and with which the manifolds are in contact.

For the three-to-one manifold 32, these supports include a mounting clip 78 within which the portion of the manifold 32 to which tube 52 connects is mounted. This clip 78, shown in the isolated illustrative view of FIG. 12A, is shaped much like the mounting clips 62 of the tubes 46, 48, 51, 52, but has a wider mouth to accommodate the port of the manifold 32. In addition, the clip 78 is connected only to the surface of the cassette rather than being formed from one of the ribs 64 or edges of the cassette 24. The sides of the mounting clip 78 give slightly when the manifold 32 is pressed into place, allowing the manifold to be received and held in the semicircular region of the clip 78.

The portions of the manifold 32 which connect to tubes 48, 50, and 34 each rest on a semicircular projection 80 from the cassette surface to keep them at the proper distance from the top surface of the cassette 24. An example of these projections 80 is illustrated in the isolated illustrative side view of FIG. 12B. A semicircular projection 80 is also used to support the portion of manifold 36 which connects to tube 34. The other side of the one-to-one manifold 36 is supported by a mounting clips 62 formed in one of ribs 64.

In addition to the portions of the cassette which support the manifolds 32, 36 and tubes 46, 48, 51, 52, each of horizontal closing surfaces (anvils) 82 shown in FIG. 9 provides a rigid, flat contact surface against which a tube may be pinched closed. The anvils 82 are formed on the cassette 24 during the molding process, and are each wide enough to accommodate a flexible tube when it has been spread out in one direction from being pinched closed (occluded).

D. Valves

Figure 13:
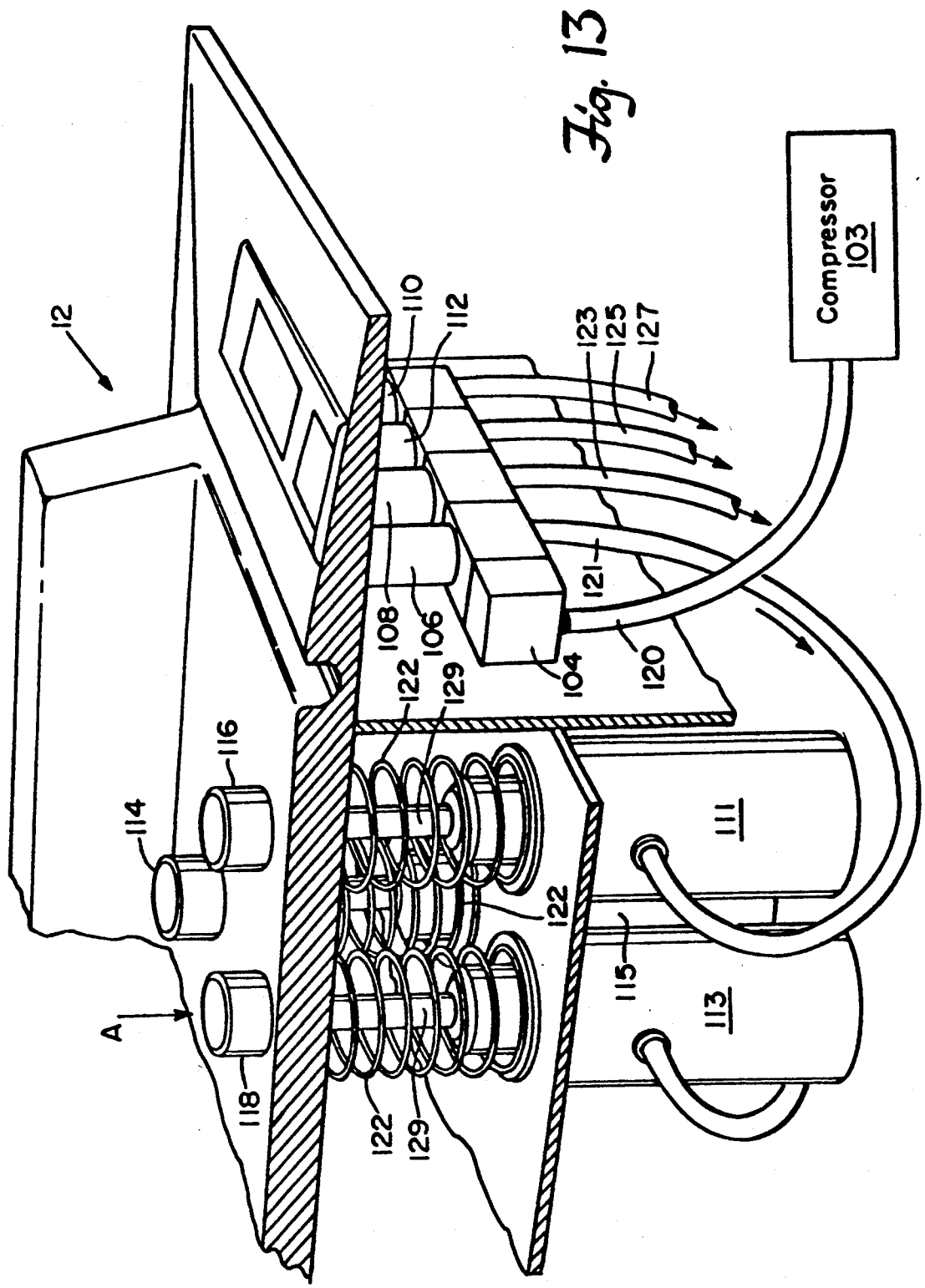
FIG. 13 is a detailed perspective view of the pinch valves.

Referring to FIG. 13, which is a detailed perspective view of a portion of the deck assembly 12, pinch valves 114, 116, 118 are shown which control fluid flow through the cassette 24. The pinch valves 114, 116, 118 are arranged in a triangular array, to coordinate with the closing surfaces 82 of the cassette 24 (FIG. 8), when the cassette 24 is in place on deck assembly 12. The pinch valves 114, 1161 118 are rigid, cylindrical members, the movement of which is controlled by the activation and deactivation of solenoid valves 106, 108, 110.

A solenoid valve manifold housing 104 has output lines 121, 123, 125 through which pressure is vented to respective pinch valve cylinders 111, 113 and 115. Compressed air from an air compressor 103 (shown schematically) is input to solenoid valve manifold housing 104 through conduit 120. No air from the compressor reaches a pinch valve cylinder until its corresponding solenoid valve is actuated. Actuation of a solenoid valve moves the associated solenoid out of the flow path within housing 104, allowing air pressure through to the desired pinch valve.

Pressure is delivered from the compressor 103 to the solenoid manifold housing 104. The venting of pressure through a particular solenoid valve is controlled from controller 500 by electronically activating the solenoid corresponding to the desired valve. Air pressure is input to a pinch valve from the solenoid valve corresponding to the pinch valve shown. Each pinch valve is held in a normally closed position by a spring 122. The force of the spring 122 compresses the valve into its respective tube, closing it against a closing surface 82 of the cassette 24. When the solenoid valve for a pinch valve is opened, it valves fluid pressure through the solenoid valve housing 104 to the air cylinder chamber of the pinch valve. This pressure forces the piston 129 of the valve down (i.e. in the direction of arrow A), lowering the piston 129 and compressing the corresponding spring 122.

The lowering of the piston 129 results in the opening of the pinch valve and the allowance of fluid flow through the tube controlled by the pinch valve. An identical arrangement is provided for each of the pinch valves 114, 116, 118 of the present invention. Each of the pinch valve springs are biased by the springs 122 to keep the pinch valves in an upward position normally occluding flow. Therefore a power loss to the system results in the sealing of all fluid flow through the cassette 24, rather than an opening of all the fluid lines. This prevents any undesired leakage of fluid through the tubes.

With a cassette 24 in place on the deck assembly, and the handle 18 closed to hold the cassette 24 in place, each pinch valve 114, 116, 118 is aligned such that the spring tension of the valve forces it to compress the tube with which it is aligned against a closing surface 82 of the cassette 24. The compression of a tube by its pinch valve is sufficiently extensive to stop the flow of fluid through the tube. Thus, the pinch valves control fluid flow through the tubes of the cassette 24 without physically contacting the fluids in the tubes.

The handle 18 of the deck assembly 12 is instrumental in moving the drag bar 94 to the cassette 24 in place on surface 14, but is also part of a mechanism for raising and lowering elements intended to protrude through the surface 14 of the deck assembly 12 when the handle is in the lowered position. For example, the pinch valves 114, 116, 118 are normally closed, and therefore normally protrude through the surface 14 of the deck assembly 12. However, when the cassette 24 must be removed from the deck assembly 12, it is desirable to have the pinch valves and the fluid detector sensor 117 (not shown) recessed below the surface 14 so that the cassette 24 may be slid easily out of the deck assembly 12.

E. Housing

Figure 14:
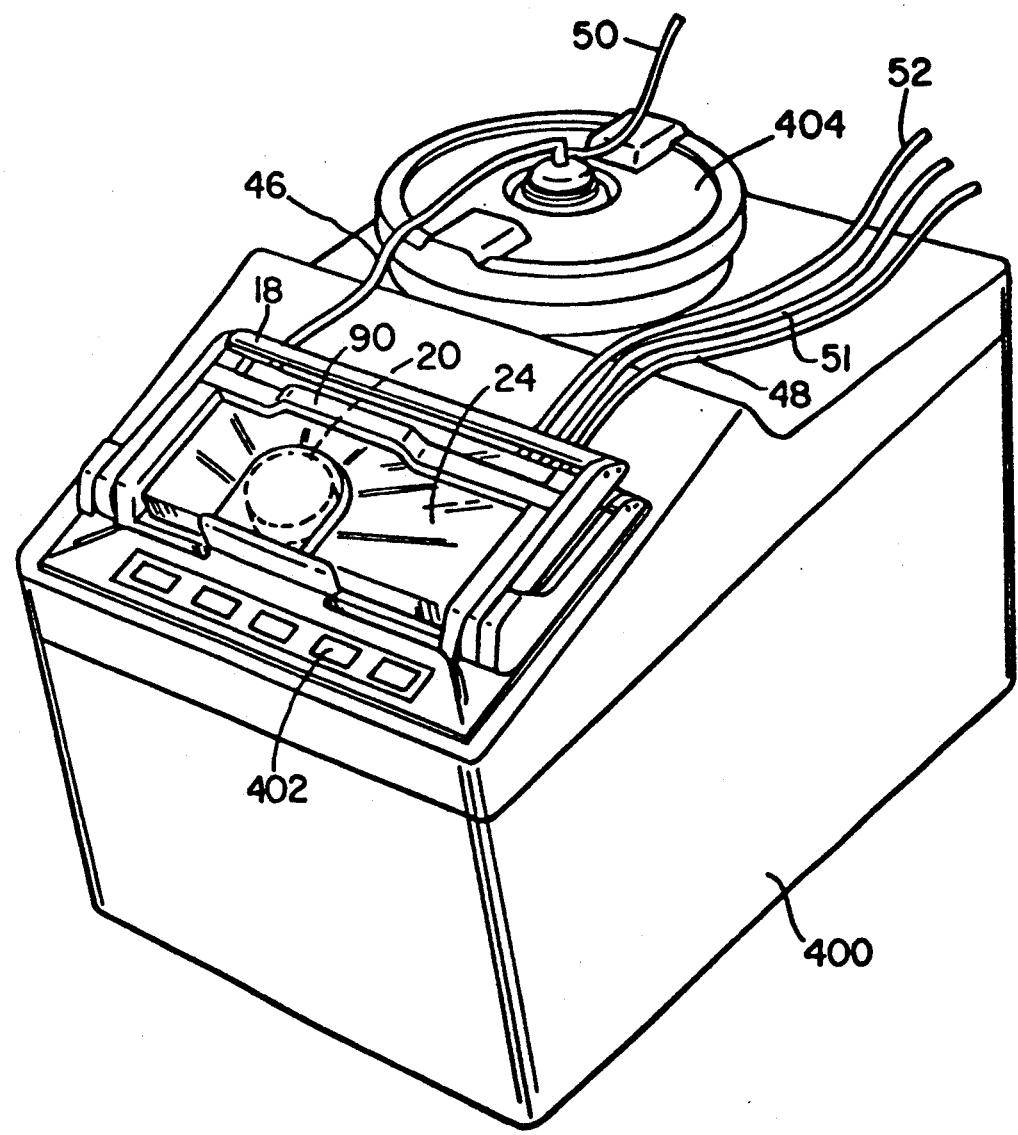
FIG. 14 is a perspective view of a blood washing apparatus associated with the present invention.

FIG. 14 shows the processing unit mounted in a housing 400. As shown, the deck assembly is positioned with the control panel 402 in the front of the housing. Thus, handle 18 opens toward the front of the housing and the cassette 24 slides in under the handle 18 and toward the front of the housing 400. Tube 46 leads to centrifuge 40 which is located in centrifuge housing 404.

Tubes 48, 50, 51 and 52 lead to shed blood reservoir 54, wash solution bag 56, reinfusion bag 58 and waste bag 57, respectively (FIG. 1). When the cassette 24 is loaded, and all fluid connections are closed, a fill/wash-/empty cycle may begin. The controller 500 (FIG. 1) opens valve 112 to lock the pneumatic handle locking mechanism, and the sequence begins, as discussed previously.

F. Pump

Figure 15A:
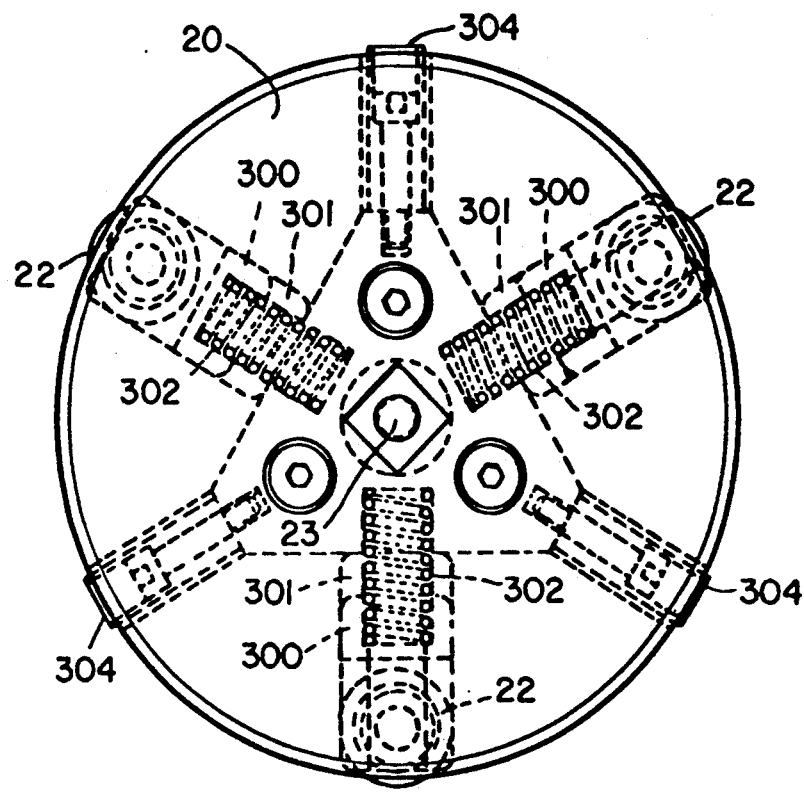
FIG. 15A is a cross section of a pump rotor of the deck module assembly of FIG. 2.
Figure 15B:
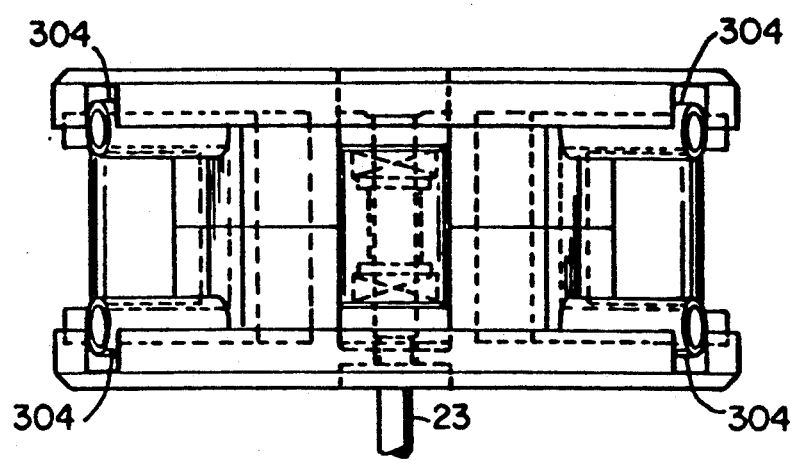
FIG. 15B is a detailed side view of the pump rotor of FIG. 15A.

The pump rotor 20 is shown in more detail in FIGS. 15A and 15B. Each of rollers 22 is mounted in a roller carriage housing 300 which is spring-loaded by a spring 302. Each spring 302 forces its roller carriage outward in a radial direction away from the shaft 23 which connects the rotor 20 to the pump motor 21. A locking connection exists between each spring 302 and its accompanying carriage 300, as well as between each spring and the body of the rotor 20. Each roller carriage 300 slides within a slot 301 in the body of the rotor 20.

As mentioned, the rollers are spaced 120° apart about the circumference of the rotor 20. In the preferred embodiment, the platen 60 of the cassette 24 forms an arc of 122°.

Also housed in rotor 20 are three pairs of tubing guide rollers 304. As shown in the detailed side view of FIG. 15B, the guide rollers 304 are positioned to receive tube 34 between the two guide rollers of a pair. The bearings are cylindrically shaped, and are each free to rotate along their cylindrical axis. The guide rollers serve to reduce wear on the tube 34 due to contact with the rotating rotor 20.

G. Fluid Sensor

A fluid sensor 117 in the form of an ultrasonic transducer is mounted on base plate 134 for retractable insertion into an opening provided in deck 14, as shown in FIG. 16. The sensor 117 determines the presence of fluid in manifold 36 using echo-sounding principles to detect the difference in time of travel through air versus fluid.

With the cassette 24 in the locked operating position, as shown in FIG. 16, base plate 134 is in its highest vertical position. When this position is reached, the fluid sensor 117 comes into intimate contact with a flat coupling surface 450 formed on manifold 36. Coupling surface 450 is formed opposite three flat reflective surfaces 456, 454, 452, formed on the exterior, far interior, and near exterior surfaces, respectively, of manifold 36 (as shown in detail in FIGS. 17–20).

The coupling force between fluid sensor 117 and surface 450 is established by spring 458.

Fluid sensor 117 detects the presence of fluids in manifold 36 and feeds an appropriate signal to controller 500 of FIG. 1. Once fluid is sensed in place of air in manifold 36, the controller 500 can calculate volume processed by counting the number of revolutions of rotor 20.

While the invention has been particularly shown and described with reference to a preferred embodiment thereof, it will be understood by those skilled in the art that various changes in form and details may be made therein without departing from the spirit and scope of the invention as defined by the appended claims. For example, the fluid flow apparatus is not limited to use during a blood washing closed circuit fluid control, any medical procedures which require sterilization to be maintained in fluid conduits, can benefit from the present invention. In addition, the two-piece peristaltic pump of the present invention may be applied to other fluid flow applications in which having the compressing rollers on the inside of the pump platen is advantageous. Hydraulic actuators may be used in place of the pneumatic system described herein.

We claim:

1. A blood-processing apparatus for providing failsafe control of fluid transfer between a primary tube and a plurality of secondary tubes with which the primary tube is in fluid communication, the apparatus comprising:
   a cassette to which the secondary tubes are mounted, each secondary tube being mounted adjacent a closing surface;
   a working surface to which the cassette is removably secured; and
   a plurality of pinch valves each of which controls occlusion of one of the secondary tubes, the pinch valves being biased in a normally-closed position such that absent electrical power to the apparatus and with the cassette secured to the working surface, each pinch valve compresses a secondary tube against a closing surface to restrict fluid flow therethrough.

2. An apparatus according to claim 1 wherein the pinch valves protrude through the working surface.

3. An apparatus according to claim 1 further comprising a securing mechanism by which the cassette is removably secured to the working surface, the securing mechanism being linked to motion of the pinch valves such that with the cassette located adjacent the working surface, operation of the securing mechanism to secure the cassette to the working surface causes the pinch valves to extend toward the cassette to engage the secondary tubes and the primary tube being coupled at one end to a manifold having a transparent surface to permit detection of fluid in the manifold by a fluid sensor.

4. A blood-processing apparatus for providing failsafe control of fluid transfer between a primary tube and a plurality of secondary tubes with which the primary tube is in fluid communication, the apparatus comprising:
   a cassette to which the secondary tubes are mounted, a first manifold coupling each secondary tube to the primary tube and a second manifold coupling another tube to the primary tube, each secondary tube being mounted adjacent a closing surface;
   a working surface to which the cassette is removably secured;
   a plurality of pinch valves each of which controls occlusion of one of the secondary tubes, the pinch valves being biased in a normally-closed position such that with the cassette secured to the working surface, each pinch valve compresses a secondary tube against a closing surface to restrict fluid flow therethrough;
   a movable handle which, when closed, causes the cassette to be secured to the working surface;
   a base plate to which the pinch valves are mounted;
   a lifting mechanism linking motion of the base plate in a direction perpendicular to the plane of the working surface to motion of the handle, closing of the handle moving the base plate closer to the working surface such that the pinch valves extend through spaces in the working surface to engage the secondary tubes of the cassette mounted to the working surface; and a locking mechanism which, if locked when the handle is in a closed position, restricts the motion of the handle and the lifting mechanism to prevent motion of the handle away from the closed position while the blood-processing apparatus is being operated; and a fluid sensor for monitoring the presence of fluid in the second manifold.

5. An apparatus according to claim 4 wherein the lifting mechanism comprises a cam which rotates with rotation of the handle and a cam rod secured to the base plate, the cam rod having a surface which contacts a surface of the cam such that rotation of the cam causes said cam surface to move relative to said cam rod surface to change the vertical position of the cam rod and the base plate relative to the working surface.

6. Apparatus for processing of blood fluids comprising:
   a) a first flexible fluid communication tube coupled between first and second rigid fluid manifolds;
   b) said first manifold having an external flat sonic coupling surface for coupling radiation from an external transducer into and out of the manifold for sensing the presence of fluid in the manifold.

7. The apparatus of claim 6 wherein the manifold is generally tubular in shape except where the flat surface is located.

8. The apparatus of claim 7 wherein the flat coupling surface is formed opposite three flat reflective surfaces formed respectively on the exterior, far interior and near interior surfaces of the manifold.

9. The apparatus of claim 6 wherein the radiation is sound radiation.

10. The apparatus of claim 9 wherein the sound radiation is in the ultrasonic range.

11. A disposable assembly for use with an apparatus which regulates the flow of biological fluids, the assembly comprising:
   a first tube;
   a plurality of secondary tubes;
   an interconnection manifold for providing fluid communication between the first tube and the secondary tubes;
   a plurality of fluid containers, each in fluid communication with a separate one of the secondary tubes; and
   a flat radiation coupling surface formed on the exterior of the manifold for coupling radiation from an external transducer into the interior of the manifold to sense the presence of fluids therein.

12. An assembly according to claim 11 further including three flat reflective surfaces formed in said manifold opposite the coupling surface.

13. An assembly according to claim 11 wherein the manifold is an injection-molded structure.

14. An assembly according to claim 11 wherein the manifold is comprised of a generally tubular rigid member coupled at one end to the first tube and at another end to a secondary tube.

15. The assembly of claim 11 wherein the radiation is sound radiation.

16. The assembly of claim 15 in which the sound radiation is in the ultrasonic range.

17. Apparatus for a disposable cassette in which a rigid fluid manifold is provided for interconnecting a first flexible conduit to a second flexible conduit comprising:
   a) a planar deck for supporting said cassette in a horizontal position;
   b) a base plate depending from the deck and adapted for vertical movement from a lower plane position to an upper plane position parallel to said planar deck; and
   c) a fluid detector affixed to said base plate opposite an opening in said deck adjacent said manifold; such that when said base plate is in said upper plane position the detector is in intimate contact with a surface of the manifold.

18. The apparatus of claim 17 including mechanical base means disposed between the detector and the base plate for controlling the coupling force between the detector and the manifold surface.

19. The apparatus of claim 17 wherein the sensor is a sonic sensor which detects the presence of fluid in the manifold by detecting the difference in time of travel of a sonic signal in air versus in fluid.

20. The apparatus of claim 17 further including pinch valves mounted on the base plate for controlling the flow of fluid through the flexible conduits.

21. The apparatus of claim 20 wherein the pinch valves are biased in a normally closed position such that each pinch valve compresses a respective conduit against a surface via openings provided in the deck.

22. A blood processing system comprising:
   a) a first flexible fluid communication tube coupled on one side to a rigid fluid manifold and on another side to a blood processing centrifuge in which blood fluid is separated into constituent component fluids, some of which are coupled by said tube to said manifold;
   b) said manifold having an external flat sonic coupling surface; and
   c) an external transducer for coupling sonic radiation into and out of the manifold through the coupling surface for sensing the presence of fluid in the manifold.

23. The system of claim 22 in which the manifold is mounted on a fixed deck and the transducer on a translatable base plate such that the transducer may be moved into and out of contact with the coupling surface.

* * * * *